United States Patent
Frenkel et al.

(10) Patent No.: US 9,587,088 B2
(45) Date of Patent: Mar. 7, 2017

(54) HEAT STABILIZER FOR HALOGEN-CONTAINING POLYMERS

(71) Applicant: Galata Chemicals LLC, Southbury, CT (US)

(72) Inventors: Peter Frenkel, Danbury, CT (US); Michael Denoux, Metairie, LA (US); Garrett Mineo, Marrero, LA (US); Joseph Anthony Di Maio, Woodbury, CT (US)

(73) Assignee: Galata Chemicals LLC, Southbury, CT (US)

( * ) Notice: Subject to any disclaimer, the term of this patent is extended or adjusted under 35 U.S.C. 154(b) by 0 days.

(21) Appl. No.: 14/910,627

(22) PCT Filed: Jul. 15, 2014

(86) PCT No.: PCT/US2014/046743
§ 371 (c)(1),
(2) Date: Feb. 5, 2016

(87) PCT Pub. No.: WO2015/020762
PCT Pub. Date: Feb. 12, 2015

(65) Prior Publication Data
US 2016/0194478 A1    Jul. 7, 2016

Related U.S. Application Data

(60) Provisional application No. 61/863,839, filed on Aug. 8, 2013.

(51) Int. Cl.
| | | |
|---|---|---|
| C08K 5/58 | (2006.01) | |
| C08K 5/37 | (2006.01) | |
| C09K 15/12 | (2006.01) | |
| C09K 15/32 | (2006.01) | |
| C07F 7/22 | (2006.01) | |
| C08K 5/00 | (2006.01) | |

(52) U.S. Cl.
CPC ............. *C08K 5/58* (2013.01); *C07F 7/2268* (2013.01); *C08K 5/005* (2013.01); *C08K 5/37* (2013.01); *C09K 15/12* (2013.01); *C09K 15/32* (2013.01)

(58) Field of Classification Search
CPC ............. C08K 5/58; C08K 5/005; C08K 5/37
See application file for complete search history.

(56) References Cited

U.S. PATENT DOCUMENTS

| | | | |
|---|---|---|---|
| 3,769,263 A | 10/1973 | Mayo et al. | |
| 3,925,309 A | * 12/1975 | Weisfeld | C08K 5/58 252/406 |
| 4,193,913 A | * 3/1980 | Abeler | C07F 7/2268 524/180 |
| 4,496,490 A | 1/1985 | Larkin | |
| 4,988,750 A | 1/1991 | Buschhoff et al. | |
| 8,198,352 B2 | 6/2012 | Deelman et al. | |

FOREIGN PATENT DOCUMENTS

| | | |
|---|---|---|
| EP | 1225177 A1 | 7/2002 |
| EP | 1743898 A1 | 1/2007 |
| EP | 21236549 A1 | 11/2009 |
| GB | 1 470 016 A * | 4/1977 |
| GB | 1470016 A | 4/1977 |
| GB | 1510973 A | 5/1978 |
| WO | 90/03999 A1 | 4/1990 |
| WO | WO 90/03999 A1 * | 4/1990 |

OTHER PUBLICATIONS

Wypych, George: "PVC Degradation and Stabilization", ChemTec, Toronto 2008.
Grossman, Richard F.: "Handbook of Vinyl Formulating", Second Edition; Wiley & Sons, 2008.
Wilkes, Charles E. et al.: "PVC Handbook", ISBN 3-446-22714-8, Hanser, Cincinnati 2005.
PCT International Search Report and Written Opinion dated Oct. 2, 2014 from corresponding Application No. PCT/US2014/046743.

* cited by examiner

Primary Examiner — Robert Harlan
(74) Attorney, Agent, or Firm — Dilworth IP, LLC

(57) ABSTRACT

A stabilizer composition having low volatility and high efficiency comprising: (i.) 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds; (ii.) 0.001% to 50.000% by weight of at least one mono-methyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds; (iii.) 0.001% to 10.000% by weight of at least one tri-methyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and (iv.) 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds.

20 Claims, No Drawings

HEAT STABILIZER FOR HALOGEN-CONTAINING POLYMERS

This application is the U.S. national phase of International Application PCT/US2014/046743, filed Jul. 15, 2014, claiming priority to U.S. Provisional Application No. 61/863,839, filed Aug. 8, 2013; the disclosures of International Application PCT/US2014/046743, and U.S. Provisional Application No. 61/863,839, each as filed, are incorporated herein by reference.

FIELD OF THE INVENTION

The present invention relates to organotin heat stabilizer compositions. More particularly, the present invention relates to heat stabilizer compositions for halogen-containing polymers having high efficiency and lower toxicity, containing di-, mono- and tri-alkytin compounds and a thioester.

BACKGROUND OF THE INVENTION

Halogen-containing polymers, such as polyvinylchloride (PVC), are some of the most widely used plastics in the world. PVC in particular is widely used in such applications as pipes and pipe fittings, film and sheet, flooring, cables and construction profiles. However, PVC can decompose during processing, upon heating or on prolonged exposure to sunlight due to loss of HCl from the polymer, resulting in discoloration and embrittlement. Alkyltin stabilizers are known to be particularly effective in preventing a discoloration of halogen-containing polymers at elevated temperatures, for example, "PVC Degradation and Stabilization," Wypich, George; ChemTec, Toronto 2008. "Handbook of Vinyl Formulating", $2^{nd}$ edition; Grossman, Richard F.; Wiley & Sons, 2008. "PVC Handbook"; Wilkes, Charles E., et al; Hanser, Cincinnati 2005. However, alkyltin stabilizers are also known to have varying toxicity levels, as well as differing volatility and efficiency characteristics. These features are important considerations when choosing a stabilizer since the overall toxicity is related not just to the specific amount of the stabilizer and tin used in PVC compounds but also to its volatility. This directly correlates with a level of personnel exposure during handling of the alkyltin stabilizer and processing of PVC stabilized with those materials. There is a need for halogen-containing compositions containing alkyltin heat products that are not only efficient stabilizers, but have a reduced toxicological impact.

Several approaches have been used in an effort to develop non-toxic organotin heat stabilizers suitable for halogen-containing polymers. These approaches include: A) preparation of mono-alkyltin stabilizers while minimizing the content of both di-alkyl and tri-alkyltin compounds; B) preparation of mono-/di-alkyltin mercaptoacetate ester blends, where the alkyl group contains 12 carbon atoms, and the mercaptoacetate ester ligand is obtained with n-alcohols containing 8 carbon atoms or less; and C) preparation of mono-/di-alkyltin mercaptoacetate ester blends, where the alkyl group contains 12 carbon atoms, and the mercaptoacetate ester ligand is obtained with n-alcohols containing more than 8 carbon atoms.

EP 2123659 discloses high purity mono-alkyltin compounds containing mono-alkyltin compounds of 95-99.99% purity, having 0.01-0.5% dialkyltin compounds and 0.01-0.5% tri-alkyltin compounds, and a process for making the high purity mono-alkyltin compounds. The heat stabilizers are used in chlorine-containing polymers, glass coating chemicals, catalysts and articles comprising of at least one polymer and the high purity mono-alkyltin compound.

U.S. Pat. No. 8,198,352 is a modified version of EP 2123659, where the purity of the mono-alkyltin compounds ranges from 85 to 99.999%, and the di- and tri-alkyltin compounds are present at 0.001-10% and 0.001-5%, respectively.

U.S. Pat. No. 4,496,490 discloses preparation of high purity mono-octyltin mercaptoacetate heat stabilizers starting from a mono-octyltin chloride of 99.2% purity. While the product contained up to 5% tri-octyltin iso-octylmercaptoacetate, the presence of di-octyltin compounds in the final product was not reported.

U.S. Pat. No. 4,193,913 discloses high purity mono-alkyltin stabilizers that were prepared using mono-methyl-, mono-butyl- or mono-octyltin chlorides as raw materials, and reacting those with mercaptoacetate esters. The purity of the chlorides was not specified.

EP 1743898 discloses preparation of mono- and dialkyltin chlorides. While di-octyltin chloride was obtained at a purity of greater than 98%, purity of the mono-alkyltinchloride was not measured.

EP 1225177 discloses preparation of mono-alkyltin halides at greater than 60% yield using a variety of catalysts. However, purity of the obtained products was not measured.

GB 1510973 discloses the preparation of mono-octyltin mercaptoacetate stabilizers using mono-octyltin chloride of 99.2% purity. The purity of the prepared mono-octyltin stabilizer was not measured or disclosed.

EP 2123659, U.S. Pat. Nos. 8,198,352, 4,496,490 and 4,193,913 also disclose that mono-octyltin stabilizers are of low toxicity. However, it should be noted that high purity mono-alkyltin stabilizes are of lower tin content (see Table 1), and therefore, inefficient in terms of providing adequate long-term heat stability to PVC compared with the synergistic blends containing both mono- and di-alkyltin mercaptoacetates.

TABLE 1

Calculated Tin content of selected mono- and di-2-ethylhexyl mercaptoacetates

| Mono-/di alkyltin 2-ethylhexyl mercaptoacetates | Molecular Weight | % Tin |
|---|---|---|
| Mono-methyltin tris(2-ethylhexyl mercaptoacetate) | 744 | 16.0 |
| Di-methyltin bis(2-ethylhexyl mercaptoacetate) | 555 | 21.4 |
| Mono-butyltin tris(2-ethylhexyl mercaptoacetate) | 786 | 15.1 |
| Di-butyltin bis(2-ethylhexyl mercaptoacetate) | 640 | 18.6 |
| Mono-octyltin tris(2-ethylhexyl mercaptoacetate) | 842 | 14.1 |
| Di-octyltin bis(2-ethylhexyl mercaptoacetate) | 752 | 15.8 |

U.S. Pat. No. 4,988,750 discloses preparation of a heat stabilizer comprising a 60/40 mono- and di-dodecyltin mercaptoacetate ester blend, where alcohols used for obtaining the mercaptoacetate ligand contained 8 carbon atoms.

U.S. Pat. No. 3,769,263 discloses dibutyltin mercaptoacetate and mercaptopropionate esters which were used as co-stabilizers, where the mercapto-ester ligands were obtained from alcohols containing 12 and 18 carbon atoms.

Nevertheless, a continuing need exists for organotin heat stabilizers for halogen-containing polymers having good efficiency and reduced toxicological impact during handling of the stabilizers and processing of PVC stabilized with those materials. It has unexpectedly been found that heat stabilizer compositions comprising particular blends of di-, mono- and tri-methyltin compounds and a thioester provide excellent heat stability for halogen-containing polymers, while also possessing reduced toxicological impact arising from lower volatility of the stabilizers.

SUMMARY OF THE INVENTION

In one embodiment, the invention relates to a stabilizer composition comprising: (i) 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds; (ii) 0.001% to 50.000% by weight of at least one mono-methyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds; (iii) 0.001% to 10.000% by weight of at least one tri-methyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and (iv) 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds.

In another embodiment, the invention relates to a stabilized composition comprising a stabilizer composition and a halogen-containing polymer. The stabilizer composition comprises: (i) 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds; (ii) 0.001% to 50.000% by weight of at least one mono-methyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds; (iii) 0.001% to 10.000% by weight of at least one tri-methyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and (iv) 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds, the stabilizer composition being present in an amount from 0.01 to 10 parts by weight per 100 parts by weight of the halogen-containing polymer.

In still another embodiment, the invention relates to a process comprising compounding a stabilizer composition with a halogen-containing polymer. The stabilizer composition comprises (i) 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds; (ii) 0.001% to 50.000% by weight of at least one mono-methyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds; (iii) 0.001% to 10.000% by weight of at least one tri-methyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and (iv) 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds.

DETAILED DESCRIPTION OF THE INVENTION

In one embodiment, the invention relates to a stabilizer composition comprising:

i. 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds;

ii. 0.001% to 50.000% by weight of at least one mono-methyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds;

iii. 0.001% to 10.000% by weight of at least one tri-methyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and iv. 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds.

Preferably, in the stabilizer composition, the dimethyltin compound is present in an amount from 44.500% to 93.990% by weight, the mono-methyltin compound is present in an amount from 3.000% to 40.000% by weight, the tri-methyltin compound is present in an amount from 0.010% to 0.500% by weight, and the thioester is present in an amount from 3.000% to 15.000% by weight.

Moreover, in the stabilizer composition, $R_1$, $R_2$, $R_3$, and $R_4$ are preferably saturated alkyl groups. Preferably, $R_1$, $R_2$, $R_3$, and $R_4$ are independently selected from decyl, dodecyl, tetradecyl or octadecyl. More preferably, $R_1$, $R_2$, $R_3$, and $R_4$ are the same. Most preferably, $R_1$, $R_2$, $R_3$, and $R_4$ are tetradecyl.

The stabilizer compositions of the present subject matter provide excellent volatility. Typically, the volatility of the stabilizer composition is no greater than 1.0% by weight. Preferably, the volatility of the stabilizer composition is no greater than 0.5% by weight.

The stabilizer composition of the present subject matter also demonstrates high stabilization efficiency with respect to tin content. Typically, the stabilizer composition has an on-set decomposition temperature of at least 240° C. with a total tin content of no greater than 15.0 wt. %.

In another embodiment, the present invention relates to a stabilized composition comprising:

(A) a stabilizer composition comprising:

i. 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds;

ii. 0.001% to 50.000% by weight of at least one mono-methyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds;

iii. 0.001% to 10.000% by weight of at least one trimethyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and iv. 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds; and (B) a halogen-containing polymer, the stabilizer composition being present in an amount from 0.01 to 10 parts by weight per 100 parts by weight of the halogen-containing polymer.

The components of the stabilizer composition can be blended by a variety of processes well known to those skilled in the art; for example, by melt blending, dry blending, extrusion, calendaring, molding and combinations thereof. The halogen-containing polymer and the stabilizer composition can be blended via compounding by well-known processes such as extrusion, calendaring, molding and combinations thereof. Compounding of the halogen-containing polymer and the stabilizer composition can also include first blending the components as described above followed by compounding.

Halogen-Containing Polymers

Halogen-containing polymers include homopolymers and copolymers of vinyl halogens, post-halogenated polymers and co-polymers of vinyl halogens, and halogenated polymers of olefins, such as ethylene, propylene, and 1-butene. The halogen of such polymers can be fluorine, chlorine, bromine, iodine, or mixtures thereof.

Preferably, the halogen-containing polymer is selected from polyvinyl chloride, polyvinylidene chloride, chlorinated polyvinyl chloride ("CPVC") or mixtures thereof. More preferably, the halogen-containing polymer is polyvinyl chloride. The PVC can be obtained via polymerization in bulk or in suspension, in emulsion, in micro suspension, or in suspended emulsion.

As employed herein, the term PVC is intended to include both homopolymers and copolymers of vinyl chloride, i.e., vinyl resins containing vinyl chloride units in their structure, e.g., copolymers of vinyl chloride and vinyl esters of aliphatic acids, in particular vinyl acetate; copolymers of vinyl chloride with esters of acrylic and methacrylic acid and with acrylonitrile; copolymers of vinyl chloride with diene compounds and unsaturated dicarboxylic acids or anhydrides thereof, such as copolymers of vinyl chloride with diethyl maleate, diethyl fumarate or maleic anhydride; post-chlorinated polymers and copolymers of vinyl chloride; copolymers of vinyl chloride and vinylidene chloride with unsaturated aldehydes, ketones and others, such as acrolein, crotonaldehyde, vinyl methyl ketone, vinyl methyl ether, vinyl isobutyl ether, and the like.

The term PVC as employed herein is also intended to include graft polymers of PVC with ethyl-vinyl acetate ("EVA"), acrylonitrile/butadiene-styrene ("ABS"), and meth-acrylate-butadiene ("MBS"). Preferred substrates are also mixtures of the above-mentioned homopolymers and copolymers, preferably vinyl chloride homopolymers, with other thermoplastic and/or elastomeric polymers, more preferably blends with ABS, MBS, acrylonitrile butadiene ("NBR"), styrene-acrylonitrile ("SAN"), EVA, chlorinated polyethylene ("CPE"), poly(methyl methylacrylate), ethylene propylene diene monomer ("EPDM"), and polylactones. Preferably, vinyl acetate, vinylidene dichloride, acrylonitrile, chlorofluoroethylene and/or the esters of acrylic, fumaric, maleic and/or itaconic acids are monomers that are copolymerizable with vinyl chloride.

The content of the subject stabilizer composition within the stabilized polymer composition is typically between 0.01 parts and 10 parts by weight, preferably between about 0.1 and 7.0, and more preferably between 0.25 and 5.0 parts by weight for 100 parts by weight of the halogen-containing polymer.

In still another embodiment, the present invention relates to a process comprising compounding:

(A) a stabilizer composition comprising:

i. 25.000% to 99.997% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds;

ii. 0.001% to 50.000% by weight of at least one monomethyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds;

iii. 0.001% to 10.000% by weight of at least one trimethyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and iv. 0.001% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds; and (B) a halogen-containing polymer.

Co-Stabilizers

The stabilizer compositions can additionally contain co-stabilizers. Co-stabilizers which can be present in the compositions include epoxidized soy bean oil, dihydropyridine compounds, α-phenylindole, polyols, disaccharide alcohols, perchlorate compounds, glycidyl compounds, layered lattice compounds (hydrotalcite), zeolite compounds, phosphite compounds, β-diketones, β-ketoesters, mercaptoacetic acid, mercaptocarboxylic esters, metal soaps, amino- and/or thiouracils, hydrazides, and mixtures thereof. Such co-stabilizers are well known to those skilled in the art and are exemplified in WO 2006/058789.

Examples of suitable polyols and disaccharide alcohols are pentaerythritol, dipentaerythritol, sorbitol (hexitols), glycerol, isosorbide, diglycerol, polyglycerol, and thiodiglycerol. Preferably, the polyols are disaccharide alcohols.

The polyols and/or disaccharide compounds can be present in the compositions in an amount of from 0.01 to 20, preferably from 0.1 to 20 and, more preferably, from 0.1 to 10 parts by weight per 100 parts by weight of halogen-containing polymers.

Examples of perchlorate compounds are those of formula $M(ClO_4)_n$, wherein M is Li, Na, K, Mg, Ca, Sr, Ba, Zn, Al, La or Ce. Depending on the valency of M, n is 1, 2 or 3. The perchlorate salts can be present as solutions or in the form of complexes with alcohols (polyols, cyclodextrins), ether alcohols or ester alcohols. The ester alcohols also include polyol partial esters. Other suitable solvents are phosphate esters and cyclic and acyclic carbonates. The perchlorate salts can be present as a salt or solution in water or an organic solvent, or adsorbed on a support material such as PVC, calcium silicate, zeolites or hydrotalcites; or bound by chemical reaction into a hydrotalcite or into another layered lattice compound. Preferably, the polyol is a polyol partial ether selected from glycerol monoethers, glycerol monoesters or glycerol monothioethers. Further embodiments are described in EP 0 394 547, EP 0 457 471 and WO 94/24200.

Perchlorates can be present in the compositions in an amount from 0.001 to 5, preferably from 0.01 to 3, and more preferably, from 0.01 to 2 parts by weight per 100 parts by weight of the halogen-containing polymers.

Glycidyl compounds that may be used as co-stabilizers are preferably those containing a glycidyl group directly bonded to carbon, oxygen, nitrogen or sulfur atoms. Examples include glycidyl esters and β-methylglycidyl esters or 2,2-bis(4-hydroxycyclohexyl)propane. Other epoxide compounds which can be included in the compositions are given in EP 0 506 617. Epoxy compounds having two functional groups are preferred. It is also possible to employ epoxy compounds having one, three or more functional groups. Preferably, the epoxy compounds are selected from diglycidyl compounds having aromatic groups. It is also possible to employ a mixture of different epoxy compounds. Terminal epoxy compounds to diglycidyl ethers based on bisphenols, such as on 2,2-bis(4-hydroxyphenyl)propane (bisphenol A), bis(4-hydroxyphenyl)methane or mixtures of bis(ortho/para-hydroxyphenyl)methane (bisphenol F), are preferred. The terminal epoxy compounds can be present in the compositions in an amount of at least 0.1, preferably from 0.1 to 50, more preferably from 1 to 30, and most preferably from 1 to 25 parts by weight, per 100 parts by weight of the halogen-containing polymers.

Examples of hydrotalcites that may be used as co-stabilizers are compounds known to those skilled in the art as shown, for example, in DE 384 35 81, EP 0 062 813 and WO 1993/20135.

Hydrotalcites that can be present in the compositions include those of the general formula: $M^{2+}_{1-x}M^{3+}_{x}(OH)_2$ $(An^{b-})_{x/b}dH_2O$, wherein $M^{2+}$ represents one or more metals from the group Mg, Ca, Sr, Zn and Sn, $M^{3+}$ represents Al or B, An is an anion having the valency n, b is a number from 1 to 2, $0<x<0.5$, and d is a number in the range from 0 to 300, preferably in the range from 0.5 to 30. Preferably, An is $OH^-$, $ClO_4^-$, $HCO3^-$, $CH_3COO^-$, $C_6H_5COO^-$, $CO_3^{2-}$, $(CHOHCOO)_2^{2-}$, $(CH_2COO)_2^{2-}$, $CH_3CHOHCOO^-$, $HPO_3^-$ or $HPO_4^{2-}$.

Examples of hydrotalcites are $Al_2O_3 6MgO CO_2 12H_2O$ (i), $Mg_{4.5} Al_2(OH)_{1.3} CO_2 3.5H_2O$ (ii), $4MgO Al_2O_3 CO_2 9H_2O$ (iii), $4MgO Al_2O_3 CO_2 6H_2O$, $ZnO 3MgO Al_2O_3 CO_2 8-9H_2O$ and $ZnO 3MgO Al_2O_3 CO_2 5-6H_2O$. Preferred are types i, ii and iii.

Zeolite co-stabilizers may be zeolites described by the general formula: $M_{x/n}[(AlO_2)x(SiO_2)_y]wH_2O$ wherein n is the charge of the cation M, M is an element from the first or second main group, such as Li, Na, K, Mg, Ca, Sr or Ba, y and x are numbers from 0.8 to 15, preferably from 0.8 to 1.2; and w is a number from 0 to 300, preferably from 0.5 to 30. Examples of zeolites are sodium aluminosilicates of the types zeolite A, sodalite, zeolite Y, zeolite X, zeolite LSX; or the zeolites prepared by complete or partial replacement of the Na atoms by Li, K, Mg, Ca, Sr or Zn atoms.

Preferred zeolites are zeolite A, sodalite, zeolite Y, zeolite X, and those X zeolites having an Si/Al ratio of about 1:1, called LSX for Low Silica X; or the zeolites prepared by complete or partial replacement of the Na atoms by Li, K, Mg, Ca, Sr, Ba or Zn atoms. The zeolites can be lower in water content, or anhydrous. Preferred is Na zeolite A and Na zeolite P.

The hydrotalcites and/or zeolites can be present in the compositions in an amount of from 0.1 to 20, preferably from 0.1 to 10 and more preferably from 0.1 to 5 parts by weight per 100 parts by weight of the halogen-containing polymers.

Phosphites (phosphorous triesters) that can be present in the compositions include thiophosphites and thiophosphates, triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, bis(2,4-di-tert-butyl-6-methylphenyhl) methylphenyl)methyl phosphite, and bis(2,4-di-tert-butyl-6-methylphenyl)ethyl phosphite.

Preferably, the phosphites are aryl dialkyl and alkyl diaryl phosphites such as phenyl didecyl, 2,4-di-tert-butylphenyl didodecyl phosphite, 2,6-di-tert-butylphenyl didodecyl phosphite and the dialkyl and diaryl pentaerythritol diphosphites, such as distearyl pentaerythritol diphosphite, and non-stoichiometric triaryl phosphites.

The phosphites can be present in the compositions in an amount of from 0.01 to 10, preferably from 0.05 to 5, and more preferably from 0.1 to 3 parts by weight per 100 parts by weight of halogen-containing polymers.

Examples of the β-diketones and β-keto esters that may be used in the compositions are 1,3-dicarbonyl compounds, which can be linear or cyclic dicarbonyl compounds. Examples of 1,3-dicarbonyl compounds of the above formula and their alkali metal, alkaline earth metal and zinc chelates are acetylacetone, dibenzoylmethane, and stearoylbenzoylmethane.

The 1,3-diketo compounds can be present in the compositions in an amount of from 0.01 to 10, preferably from 0.01 to 3, and more preferably from 0.01 to 2 parts by weight per 100 parts by weight of the halogen-containing polymers.

Examples of mercaptocarboxylic esters include esters of thioglycolic acid, mercaptopropionic acid, thiolactic acid, and mercaptoethanol.

Metal soaps that can be used as co-stabilizers in the compositions include metal carboxylates of relatively long-chain carboxylic acids. Examples include stearates and laurates, and oleates and salts of shorter-chain alkanecarboxylic acids. Metal soaps can also include alkylbenzoic acids. The metals can include Li, Na, K, Mg, Ca, Sr, Ba, Zn, Al, La, Ce and rare earth metals. Synergistic mixtures, such as barium/zinc, magnesium/zinc, calcium/zinc or calcium/magnesium/zinc stabilizers can also be used. The metal soaps can be used individually or in mixtures. Preferably, the metal soap can be selected from the zinc, calcium, magnesium or barium salts of monovalent carboxylic acids such as octanoic, neodecanoic, 2-ethylhexanoic, decanoic, undecanoic, dodecanoic, tridecanoic, myristic, palmitic, isostearic, stearic, 12-hydroxystearic, behenic, and sorbic acid; and calcium, magnesium and zinc salts of divalent carboxylic acids, such as oxalic, malonic, succinic, glutaric, adipic, fumaric, phthalic, isophthalic, terephthalic, hydroxyphthalic acid and citric acid.

More preferably, the metal soaps are selected from the calcium, magnesium, barium and zinc carboxylates of carboxylic acids having 7 to 18 carbon atoms. Overbased carboxylates, such as overbased zinc octoate, are also preferred. Overbased calcium or barium soaps are also preferred.

The metal soaps or metal salts can also include dimetallic salts of dicarboxylic acids such as dilithium, disodium or dipotassium salts of divalent carboxylic acids such as of oxalic, malonic, succinic, glutaric, adipic, fumaric, pentane-1,5-dicarboxylic, hexane-1,6-dicarboxylic, heptane-1,7-dicarboxylic, octane-1,8-dicarboxylic, phthalic, isophthalic and terephthalic. Preferably, the soap is disodium adipate.

Other co-stabilizers that can be present in the compositions include organic rare earth compounds, preferably compounds of the elements cerium, praseodymium, neodymium, yttrium, and mixtures thereof. More preferred are mixtures containing cerium compounds.

The metal soaps and/or mixtures thereof can be present in the compositions in an amount of from 0.001 to 10 parts by weight, preferably from 0.01 to 8 parts, and more preferably from 0.05 to 5 parts by weight per 100 parts by weight of the halogenated polymers.

Additives

The stabilizer compositions described above can also contain other additives, provided that the additives do not materially degrade the thermal stability imparted by the stabilizer compositions described herein. Such additives include, without limitation, light stabilizers, antioxidants, lubricants, fillers, fusion promoters, plasticizers, pigments, flame retardants, smoke suppressants, UV absorbers, chemical foaming agents, impact modifiers, antistatic agents, reinforcing agents, metal release agents, dispersants, whitening agents, gelling assistants and processing aids. These additives may be added to the resin using techniques and equipment well known to those of ordinary skill in the art.

Suitable lubricants include calcium stearate, montan wax, fatty acid esters, polyethylene waxes, chlorinated hydrocarbons, glycerol esters and combinations thereof.

Suitable fillers include titanium dioxide, calcium carbonate, kaolin, glass beads, glass fibers, talc, wood floor and mixtures thereof.

EXAMPLES

The following Examples further detail and explain preparation of the inventive heat stabilizers, and demonstrate their efficacy for preventing discoloration (caused by high shear and exposure to heat) of halogen-containing polymers, such as PVC and CPVC, and for providing a reduced toxicological impact during handling and processing due to lower volatility of the stabilizers. These examples merely illustrate the invention. Those skilled in the art will recognize many variations that are within the spirit of the invention and scope of the claims.

Control Example A1

Control example A1 is a mixture of mono-n-octyltin tris(2-ethylhexylmercaptoacetate) and di-n-octyltin bis(2-ethylhexylmercaptoacetate), commercially available from Galata Chemicals as Mark 17MOK.

Control Example A2

Control example A2 is a mixture of mono-methyltin tris(2-ethylhexylmercaptoacetate) and dimethyltin bis(2-ethylhexylmercaptoacetate), commercially available from Galata Chemicals as Mark 1900.

Control Example A3

Control example A3 is a low-volatility mixture of mono-methyltin tris(2-ethylhexylmercaptoacetate) and dimethyltin bis(2-ethylhexylmercaptoacetate), commercially available from Galata Chemicals as Mark 1984.

Control Example A4

Control example A4 is a mixture of di-n-butyltin bis(2-ethylhexylmercaptoacetate) and mono-n-butyltin tris(2-ethylhexylmercaptoacetate), commercially available from Galata Chemicals as Mark 292.

Examples B1-B5

Preparation of Stabilizers

Preparation of Tetradecylmercaptoacetate

Mercaptoacetic acid (100.0 g; purity 95.5%), and tetradecyl alcohol (212.0 g) were reacted in the presence of a catalyst (1.0 g) under vacuum of 29.3 inches of water for 2 hours at 170-205° F. The reaction mixture was then cooled below 140° F., and 60 g of water containing 3.0 g of a 30% aqueous ammonia solution was added with good agitation. The pH of the reaction mixture was then adjusted to 7 using 30% aqueous ammonia, and the mixture was heated back to 140° F. and allowed to settle. The aqueous layer was decanted, and the product layer was dried under vacuum at 29.5 inches water at 210° F., yielding a clear, water-white liquid tetra-decylmercaptoacetate of 98.0% purity as determined via iodometric titration.

Preparation of dimethyltin bis(tetradecylmercaptoacetate)—B5

60 g of dimethytindichloride (DMT; 32.81% Cl) and 106.0 g water were placed in a beaker, and heated to 125° F. with moderate agitation to dissolve the DMT. Then, 166.0 g of tetradecyl mercaptoacetate (98.0%) was added, followed by the rapid addition of 20 g of 30% ammonia with good agitation. Additional 30% ammonia was added to reach a 6.8 pH at 150° F. The temperature of the reaction mixture was then raised to 180° F., and 106 g of hot water was added to attain a clean phase separation. Content of the reaction mixture was transferred to a separatory funnel, and the lower layer containing the product was separated into a drying flask. The product was dried under vacuum at 29 inches of water at 200° F., and filtered using a filter aid through a Buchner Funnel using a #4 Whatman paper filter. The product was a clear water-white liquid. The total tin content was 15.4%.

Samples B1, B2, B3 and B4 were prepared according to the method described for sample B5 using dimethyltin dichloride containing various amounts of mono-methyltin trichloride. Concentrations of mono-, di-, tri-methyltin tetradecylmercaptoacetate and tetradecylmercaptoacetate for samples B1-B5 are summarized in Table 2.

TABLE 2

Weight % distribution of mono-/di-/tri-methyltin tetradecylmercaptoacetate

| Example | $CH_3Sn(SCH_2COOC_{14}H_{29})_3$ | $(CH_3)_2Sn(SCH_2COOC_{14}H_{29})_2$ | $(CH_3)_3Sn(SCH_2COOC_{14}H_{29})$ | $HSCH_2COOC_{14}H_{29}$ |
|---|---|---|---|---|
| B1 | 17.77 | 75.76 | 0.02 | 6.45 |
| B2 | 28.06 | 65.47 | 0.02 | 6.45 |
| B3 | 38.35 | 55.18 | 0.02 | 6.45 |
| B4 | 23.38 | 70.15 | 0.02 | 6.45 |
| B5 | 4.68 | 88.85 | 0.02 | 6.45 |

Volatility

Physical properties such as flash point, boiling point and enthalpy of vaporization (which indicate and directly correlate with the volatility) of mono- and di-methyltin tetradecyl mercaptoacetates, were predicted on www.chemspider.com using a method of additivity. The results are summarized in Table 4.

Thermal Stability

On-set decomposition temperature as measured by thermo-gravimetric analysis (TGA) normally indicates thermal stability and volatility of organic compounds, where higher on-set temperatures represent more thermally stable and less volatile materials. TGA was performed on Q-500, a thermo-gravimetric analyzer marketed by TA Instruments.

TABLE 4

Predicted physical properties of methyltin tetradecyl mercaptoacetates

| Physical properties | $MeSn(EHTG)_3$ | $Me_2Sn(EHTG)_2$ | $MeSn(MTG)_3$ | $Me_2Sn(MTG)_2$ | $OcSn(EHTG)_3$ | $Oc_2Sn(EHTG)_2$ |
|---|---|---|---|---|---|---|
| Molecular weight | 744 | 555 | 996 | 724 | 842 | 752 |
| Flash point, °C. | 351.137 | 265.648 | 220.7 | 220.7 | 392.508 | 358.909 |
| Boiling point, °C. | 656.992 | 515.637 | 371.1 | 371.1 | 725.399 | 669.844 |
| Enthalpy of Vaporization, kJ/mol | 96.73 | 78.754 | 61.81 | 61.81 | 105.927 | 98.433 |

EHTG = 2-ethylhexyl mercaptoacetate
MTG = tetra-decyl mercaptoacetate
Me = methyl
Oc = octyl According to Table 4, the methyltin tetradecyl mercaptoacetates were predicted to be of lower flash point, lower boiling point and lower enthalpy of vaporization, and therefore expected to be more volatile than the corresponding conventional methyltin 2-ethylhexyl mercaptoacetates and octyltin 2-ethylhexyl mercaptoacetates.

The volatility of the inventive stabilizers was then measured relative to conventional stabilizers as percent of weight loss at 160° C. over 10 minutes. For that purpose, a 2 g sample of each organotin stabilizer was placed on a drying balance (Mettler; Model PM400/LP16) equilibrated at 160° C. The measurements were taken in triplicate, and average values are shown in Table 5.

TABLE 5

Measured Volatility of selected organotin stabilizers

| Organotin Stabilizers | % Volatiles |
|---|---|
| A1 | 2.5 |
| A2 | 1.5 |
| B2 | 0.3 |

Contrary to the predicted data of Table 4, sample B2 unexpectedly demonstrated volatility that was 80-88% lower than that of the conventional methyltin- and octyltin 2-ethyhexyl mercaptoacetate stabilizer blends. Due to the lower volatility, the inventive stabilizer B2 should result in a reduced toxicological impact during handling and processing.

Samples of organotin stabilizers were equilibrated at 30° C., and the temperature was ramped up to 600° C. at the rate of 10° C./Min. The results are shown in Table 6.

TABLE 6

On-set decomposition temperature of stabilizers

| Organotin Stabilizers | On-set decomposition temperature, °C. |
|---|---|
| A1 | 224.1 |
| A2 | 223.8 |
| B1 | 246.7 |
| B4 | 242.9 |

According to the TGA data (Table 6), examples B1 and B4 were found to be more thermally stable (by at least 19° C.) than conventional methyl- and octyltin stabilizer controls A1 and A2, and therefore, less volatile. Due to their lower volatility, stabilizers of the present subject matter lower the level of personnel exposure during handling of these stabilizers and processing of PVC stabilized with those materials, thereby corresponding to a reduced toxicological impact.

The total tin content (measured via the HBr titration method) of the A1 and A2 controls, as well as B1 and B4, are shown in Table 7. These show that the inventive stabilizers are of lower total tin content by about 8-10% compared with the controls. Usually, the efficiency of heat stabilizers directly correlate with their total tin content, so that in order to match heat stabilizing performance of a control, stabilizers of lower total tin content need to be added to a polymeric material at higher loadings to attain the same tin concentration in the polymer.

TABLE 7

Total tin content of selected stabilizers

|  | A1 | A2 | B1 | B4 |
|---|---|---|---|---|
| Tin Content, % | 16.0 | 19.2 | 14.7 | 14.4 |

Control Examples 1 and 2, and Examples 3-5

Compounded Blends of a Heat Stabilizer Composition with a Halogen-Containing Polymer Static Heat Stability Static heat stability of PVC compositions containing various stabilizers was determined by milling the compositions into sheets. These PVC compositions are shown in Table 8, where "phr", stands for parts of additives per hundred parts of PVC resin.

TABLE 8

Tested rigid PVC compounds

| Components | Manufacturer | Loading, phr |
|---|---|---|
| PVC, K = 60 (Axiall 2079) | Axiall | 100.0 |
| MBS[1] Modifier (Kane ACE B 521) | Kaneka | 6.0 |
| K 175 (processing aid) | Kaneka | 1.2 |
| Loxiol P 1141 (or G 11, G 13) | Emery Oleochemicals | 1.0 |
| Loxiol G 74 (use G 70S) | Emery Oleochemicals | 0.5 |
| Stabilizer |  | 1.2 |

[1]Methylmethacrylate-Butadiene-Styrene Copolymer

Control Example 1 was prepared using 1.2 phr of stabilizer A1. Control Example 2 was prepared using 1.2 phr of stabilizer A2. Examples 3, 4, and 5 were prepared using 1.2 phr of stabilizers B1, B4, and B2, respectively.

A sheet was prepared from Control Example 1 under standardized conditions using a two-roll mill (Dr. Collin GmbH, Ebersberg, Germany). The gap between the rolls was about 0.5 mm, and the temperature of the rolls was 165° C. The time for preparation and homogenization was 5 minutes. Sheet thickness was 0.5 mm. The PVC sheet was continuously moved from the two sides to the center, and the enlargement thus obtained was distributed over the gap with a wooden spatula over the roll with intensive homogenization of all components. Sheets were also prepared as with Control Example 1 using the material of Examples 3 and 4, and the Yellowness Index was measured.

Measurement of Yellowness Index 15 mm wide strips were cut from each milled sheet such that eight rectangular samples (15 mm×10 mm) from each sheet were produced. The samples were placed into an oven (Blue M Company, New Columbia, Pa., USA) operating at a specified temperature for thermal aging. The samples were removed from the oven at the rate of one sample every ten minutes. The assessment of thermal stability of the flexible PVC formulations was carried out by the determination of discoloration due to degradation. The Yellowness Index (ASTM D 1925-70 Yellowness Index of plastics) was measured and recorded for each sample using the microprocessor-controlled Hunterlab Labscan Spectro Colorimeter, Type 5100. Stabilizers and their respective quantities used in the tested compounds are listed in Table 9. The results of the thermal stability assessment are summarized in Table 10. A lower number represents yellow color of lower intensity, and therefore better heat stabilizing performance of the stabilizer.

TABLE 9

Stabilizers and their quantities used in tested compounds for static heat stability

|  | Control Ex. 1 | Example 3 | Example 4 |
|---|---|---|---|
| Wt. stabilizer loaded, phr | 1.2 | 1.2 | 1.2 |
| Tin content loaded with stabilizers, g | 0.1920 | 0.1764 | 0.1728 |

TABLE 10

Static Heat Stability of PVC at 190° C. (Expressed in Yellowness Index)

| Heat Exposure Time, min. | Control Ex. 1 | Example 3 | Example 4 |
|---|---|---|---|
| 0 | 13.83 | 13.18 | 11.46 |
| 10 | 16.88 | 15.01 | 13.47 |
| 20 | 21.89 | 18.82 | 17.69 |
| 30 | 37.52 | 32.36 | 32.75 |
| 40 | 94.79 | 89.86 | 84.84 |

As can be seen from Table 10, Examples 3 and 4 demonstrated excellent heat stability performance. In fact, the heat stabilizer compositions of Examples 3 and 4 provided superior heat stability at the same stabilizer loading and lower tin content relative to that of Control Example 1, as measured by the lower Yellowness Index. This shows high stabilizer efficiency of the inventive heat stabilizer compositions relative to the conventional stabilizer A1. The superior efficiency should result in an 8-10% reduction of tin content in the compound to achieve equivalent performance with A1.

Dynamic Heat Stability

The subject stabilizers were also tested in compounds described in Table 10 using the dynamic heat stability method ASTM E313 for determining the decomposition time. Each PVC compound test sample was placed into a Brabender mixer operated at 190° C. and 60 RPM. The data of Table 11 shows that stabilizers of the present invention resulted in decomposition and fusion times equivalent to or better than that of the conventional stabilizer controls.

TABLE 11

Decomposition time (Dynamic Heat Stability Method)

| Parameters | Control Ex. 1 | Control Ex. 2 | Ex. 3 | Ex. 4 | Ex. 5 |
|---|---|---|---|---|---|
| Decomposition Time, sec. | 744 | 900 | 736 | 924 | 744 |
| Fusion time, sec. | 22 | 18 | 20 | 18 | 22 |

Mill Stability (Continuous Rolling Test)

The Mill Stability Test is used to evaluate the performance of heat stabilizers when in addition to thermal exposure it is also critical to simulate dynamic stress conditions associated with a particular application, such as rigid PVC calendared film. The test was run using the two-roll mill described above in the Static Heat Stability test section. The temperature of the rolls was set at 177° C., and the weight of tested compounds was 170 g (amounts of stabilizers used are in Table 12). Test samples (2 cm×2 cm) were taken every 10 min and the YI was measured using Hunterlab Labscan Spectro Colorimeter, Type 5100. The test ended when the compounds began to stick to the rolls or became strongly discolored or decomposed. The test results are in Table 13.

TABLE 12

Stabilizers and their quantities used in tested compounds for mill stability

| | Control Ex. 1 | Control Ex. 2 | Ex. 3 | Ex. 4 |
|---|---|---|---|---|
| Wt. stabilizer Loaded, phr | 1.2 | 1.2 | 1.2 | 1.2 |
| Tin content loaded with stabilizers, g | 0.1920 | 0.2304 | 0.1764 | 0.1728 |

TABLE 13

Mill Stability Test at 177° C. (Expressed in Yellowness Index)

| Heat Exposure Time, min | Control Ex. 1 | Control Ex. 2 | Ex. 3 | Ex. 4 |
|---|---|---|---|---|
| 10 | 11.05 | 11.32 | 17.38 | 10.15 |
| 20 | 55.45 | 91.62 | 114.87 | 28.06 |
| 30 | 104.38 | 92.44 | 123.69 | 108.11 |

As can be seen from Table 13, stabilizer compositions B1 (example 3) and B4 (example 4) demonstrate excellent mill stability characteristics. Surprisingly, composition B4 resulted in superior initial mill stability (lower Yellowness Index values 10.15 and 28.06 at heat exposure times of 0 and 10 minutes) relative to the A1 and A2 controls, while being loaded at the same weight level of 1.2 phr (as opposed to the same tin level) and lower total tin content (as per Table 7 and 12). This demonstrates the higher efficiency of stabilizers of the present subject matter compared to the A1 and A2 controls, and should result in a 10-25% reduction of tin content in the PVC compound.

Dynamic Heat Stability of CPVC

The subject stabilizers also improved heat stability of CPVC as measured using the dynamic heat stability (method ASTM E313) and expressed in yellowness index (YI) and the decomposition time. CPVC formulations were prepared in accordance with Table 14. The stabilizers were loaded at the same weight level of 1.5 phr. Each CPVC compound test sample was placed in a Brabender mixer operated at 190° C. and 40 RPM. Sample chips were taken every three minutes. Color stability of the CPVC was determined using a Hunter Lab colorimeter measuring Yellowness Index (YI) of the sample chips. Lower YI signifies lower discoloration, and therefore, superior thermal stabilization against thermal decomposition. Results of the dynamic heat stability of CPVC are shown in Table 15.

TABLE 14

Tested CPVC Compounds

| Components | Manufacturer | Loading, phr |
|---|---|---|
| CPVC (Kaneka H829) | Kaneka | 100 |
| RL-165 (lubricant) | Honeywell | 0.6 |
| Loxiol G-30 | Emery | 0.4 |
| AC 629A | Honeywell | 0.4 |
| AC 316A | Honeywell | 0.1 |

TABLE 14-continued

Tested CPVC Compounds

| Components | Manufacturer | Loading, phr |
|---|---|---|
| TiO2 | DuPont | 1.0 |
| Stabilizer | See Table 13 | 1.5 |

TABLE 15

Dynamic Heat Stability Test on CPVC

| Heat Exposure Time, min | A4 | A2 | B5 | B4 |
|---|---|---|---|---|
| 3 | 27.26 | 26.44 | 20.26 | 23.96 |
| 6 | 32.49 | 52.56 | 28.12 | 30.19 |
| 9 | 48.74 | | 53.12 | 49.56 |
| Decomposition Time, min:sec | 11:00 | 7:40 | 11:52 | 11:32 |

According to the data in Table 15, stabilizers B4 and B5 resulted in equivalent or better heat stability of CPVC compounds based on Yellowness Index, while markedly extending the decomposition time.

Other features, advantages and embodiments of the invention disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed.

We claim:

1. A stabilizer composition comprising:
   i. 44.500% to 93.990% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds;
   ii. 3.000% to 40.000% by weight of at least one monomethyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds;
   iii. 0.010% to 0.500% by weight of at least one trimethyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and
   iv. 3.000% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds.

2. The stabilizer composition of claim 1 wherein $R_1$, $R_2$, $R_3$, and $R_4$ are saturated alkyl groups.

3. The stabilizer composition of claim 2 wherein $R_1$, $R_2$, $R_3$, and $R_4$ are independently selected from decyl, dodecyl, tetradecyl or octadecyl.

4. The stabilizer composition of claim 1 wherein m, n, p, and q are 1.

5. The stabilizer composition of claim 1 wherein m, n, p, and q are 2.

6. The stabilizer composition of claim 2, wherein $R_1$, $R_2$, $R_3$, and $R_4$ are the same.

7. The stabilizer composition of claim 6, wherein $R_1$, $R_2$, $R_3$, and $R_4$ are tetradecyl.

8. The stabilizer composition of claim 1 further comprising a co-stabilizer selected from epoxidized soy bean oil, dihydropyridine compounds, pyridine derivatives, polyols, disaccharide alcohols, perchlorate compounds, glycidyl compounds, hydrotalcites, zeolite compounds, phosphite compounds, β-diketones β-ketoesters, metal soaps, amino- and/or thiouracils, hydrazides or mixtures thereof.

9. The stabilizer composition of claim 1 further comprising an additive selected from light stabilizers, antioxidants, lubricants, fillers, fusion promoters, plasticizers, pigments, flame retardants, smoke suppressants, UV absorbers, chemical foaming agents, impact modifiers, processing aids, antistatic agents, reinforcing agents, metal release agents, dispersants, whitening agents, gelling assistants, or mixtures thereof.

10. The stabilizer composition of claim 1 having a volatility of no greater than 1.0% by weight.

11. The stabilizer composition of claim 1 having an on-set decomposition temperature of at least 240° C. and a total tin content of no greater than 15.0 wt. %.

12. A stabilized composition comprising:
(A) a stabilizer composition comprising:
  i. 44.500% to 93.990% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds;
  ii. 3.000% to 40.000% by weight of at least one monomethyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds;
  iii. 0.010% to 0.500% by weight of at least one trimethyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and
  iv. 3.000% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds; and
(B) a halogen-containing polymer, the stabilizer composition being present in an amount from 0.01 to 10 parts by weight per 100 parts by weight of the halogen-containing polymer.

13. The stabilized polymer composition of claim 12, wherein the stabilizer composition is present in an amount from 0.1 to 7.0 parts by weight per 100 parts by weight of the halogen-containing polymer.

14. The stabilized polymer composition of claim 13, wherein the stabilizer composition is present in an amount from 0.25 to 3.0 parts by weight per 100 parts by weight of the halogen-containing polymer.

15. The stabilized polymer composition of claim 12 wherein the halogen-containing polymer is selected from polyvinyl chloride, polyvinylidene chloride, chlorinated polyvinyl chloride or mixtures thereof.

16. A process comprising compounding (A) a stabilizer composition comprising:
  i. 44.500% to 93.990% by weight of at least one dimethyltin compound of formula $(CH_3)_2Sn(S(CH_2)_mCOOR_1)_2$ wherein $R_1$ is a linear, branched or cyclic $C_{10}$-$C_{20}$ alkyl group and m is 1 or 2, optionally containing unsaturations in the form of double or triple bonds;
  ii. 3.000% to 40.000% by weight of at least one monomethyltin compound of formula $CH_3Sn(S(CH_2)_nCOOR_2)_3$ wherein $R_2$ is a linear, branched or cyclic $C_{10}$-$C_{20}$ alkyl group and n is 1 or 2, optionally containing unsaturations in the form of double or triple bonds;
  iii. 0.010% to 0.500% by weight of at least one trimethyltin compound of formula $(CH_3)_3Sn(S(CH_2)_pCOOR_3)$ wherein $R_3$ is a linear, branched or cyclic $C_{10}$-$C_{20}$ alkyl group and p is 1 or 2, optionally containing unsaturations in the form of double or triple bonds; and
  iv. 3.000% to 15.000% by weight of at least one thioester of formula $HS(CH_2)_qCOOR_4$ wherein $R_4$ is a linear, branched or cyclic $C_{10}$-$C_{20}$ alkyl group and q is 1 or 2, optionally containing unsaturations in the form of double or triple bonds; and
(B) a halogen-containing polymer.

17. The process of claim 16 wherein the halogen-containing polymer is selected from polyvinyl chloride, polyvinylidene chloride, chlorinated polyvinyl chloride or mixtures thereof.

18. The process of claim 16 wherein the stabilizer composition is present in an amount from 0.01 to 10 parts by weight per 100 parts by weight of the halogen-containing polymer.

19. The process of claim 18, wherein the stabilizer composition is present in an amount from 0.1 to 7.0 parts by weight per 100 parts by weight of the halogen-containing polymer.

20. The process of claim 19, wherein the stabilizer composition is present in an amount from 0.25 to 3.0 parts by weight per 100 parts by weight of the halogen-containing polymer.

* * * * *